(12) United States Patent
Cutler et al.

(10) Patent No.: US 10,524,395 B2
(45) Date of Patent: Dec. 31, 2019

(54) ARTIFICIAL REEF DATACENTER

(71) Applicant: Microsoft Technology Licensing, LLC, Redmond, WA (US)

(72) Inventors: Benjamin F. Cutler, Seattle, WA (US); Norman Ashton Whitaker, Seattle, WA (US); Spencer G. Fowers, Duvall, WA (US); Jeffrey Alex Kramer, Redmond, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 315 days.

(21) Appl. No.: 15/167,755

(22) Filed: May 27, 2016

(65) Prior Publication Data

US 2016/0381835 A1 Dec. 29, 2016
US 2018/0352680 A9 Dec. 6, 2018

Related U.S. Application Data

(63) Continuation of application No. 14/752,669, filed on Jun. 26, 2015, now Pat. No. 9,801,313.
(Continued)

(51) Int. Cl.
*H05K 7/20* (2006.01)
*A01K 61/00* (2017.01)
(Continued)

(52) U.S. Cl.
CPC ....... *H05K 7/20836* (2013.01); *A01K 29/005* (2013.01); *A01K 61/00* (2013.01); *F25D 1/02* (2013.01); *F28D 1/022* (2013.01); *F28D 15/00* (2013.01); *G06F 1/20* (2013.01); *G08B 13/2491* (2013.01); *H05K 7/2079* (2013.01); *H05K 7/20236* (2013.01); *H05K 7/20263* (2013.01); *H05K 7/20709* (2013.01);
(Continued)

(58) Field of Classification Search
CPC .... A01K 29/005; A01K 67/033; A01K 61/70; F28D 1/022
USPC ................................................. 119/221, 219
See application file for complete search history.

(56) References Cited

U.S. PATENT DOCUMENTS 1,757,174 A   6/1930   Douglas
2,870,729 A   1/1959   Shannon et al.
(Continued)

FOREIGN PATENT DOCUMENTS

CN    0040651 A1    12/1981
CN    101048055 A   10/2007
(Continued)

OTHER PUBLICATIONS

Kramer, Dr. Sharon. "Final Technical Report: Evaluating the Potential for Marine and Hydrokinetic Devices to Act as Artifical Reefs or Fish Aggregating Devices." May 12, 2015.*
(Continued)

*Primary Examiner* — Magdalena Topolski
*Assistant Examiner* — Morgan T Barlow (57) ABSTRACT

Examples of the disclosure provide for an apparatus for actively promoting marine life. The apparatus includes a datacenter implemented in a body of water and coupled to a network, a pressure vessel that houses the datacenter, and one or more components coupled to the pressure vessel and adapted to actively promote reef life and sustain a surrounding ecosystem.

20 Claims, 7 Drawing Sheets

Related U.S. Application Data (60) Provisional application No. 62/286,964, filed on Jan. 25, 2016, provisional application No. 62/286,961, filed on Jan. 25, 2016.

(51) Int. Cl.

| | | |
|---|---|---|
| *G06F 1/20* | (2006.01) | |
| *F28D 15/00* | (2006.01) | |
| *A01K 29/00* | (2006.01) | |
| *F25D 1/02* | (2006.01) | |
| *F28D 1/02* | (2006.01) | |
| *G08B 13/24* | (2006.01) | |
| *H05K 7/14* | (2006.01) | |
| *A01K 67/033* | (2006.01) | |
| *F28D 21/00* | (2006.01) | |

(52) U.S. Cl.
CPC ........ *H05K 7/20745* (2013.01); *A01K 67/033* (2013.01); *F28D 2021/0028* (2013.01); *H05K 7/1495* (2013.01); *H05K 7/1497* (2013.01)

(56) References Cited

U.S. PATENT DOCUMENTS

| | | | |
|---|---|---|---|
| 3,419,849 A | | 12/1968 | Anderson et al. |
| 4,411,213 A | | 10/1983 | Laukien |
| 4,781,023 A | | 11/1988 | Gordon |
| 4,862,427 A | | 8/1989 | Almagor et al. |
| 4,913,094 A | * | 4/1990 | Jones ............... A01K 61/70 119/221 |
| 5,049,004 A | | 9/1991 | Niimura |
| 5,215,406 A | * | 6/1993 | Hudson ............... E02B 3/046 405/25 |
| 5,511,504 A | | 4/1996 | Martin |
| 5,908,265 A | * | 6/1999 | Mostkoff ............... E02B 3/046 405/29 |
| 5,969,608 A | | 10/1999 | Sojdehei et al. |
| 6,020,653 A | | 2/2000 | Woodbridge et al. |
| 6,100,600 A | | 8/2000 | Pflanz |
| 6,145,584 A | * | 11/2000 | Baynes ............... F28D 15/02 165/104.19 |
| 6,186,702 B1 | | 2/2001 | Bartkowski |
| 6,559,552 B1 | | 5/2003 | Ha |
| 6,765,487 B1 | | 7/2004 | Holmes et al. |
| 6,813,897 B1 | | 11/2004 | Bash et al. |
| 6,833,631 B2 | | 12/2004 | Van Breems |
| 6,953,328 B2 | | 10/2005 | Welch, Jr. et al. |
| 7,059,123 B2 | | 6/2006 | Welch, Jr. et al. |
| 7,105,939 B2 | | 9/2006 | Bednyak |
| 7,257,946 B2 | | 8/2007 | Welch, Jr. |
| 7,269,751 B2 | | 9/2007 | Janakiraman et al. |
| 7,453,165 B2 | | 11/2008 | Hench |
| 7,484,668 B1 | | 2/2009 | Eiler |
| 7,525,207 B2 | | 4/2009 | Clidaras et al. |
| 7,724,513 B2 | | 5/2010 | Coglitore et al. |
| 7,864,530 B1 | | 1/2011 | Hamburgen et al. |
| 8,193,651 B2 | | 6/2012 | Lightfoot et al. |
| 8,201,266 B2 | | 6/2012 | Campbell et al. |
| 8,471,397 B2 | | 6/2013 | Iglesias Rodriguez et al. |
| 8,549,869 B1 | | 10/2013 | Whitted et al. |
| 8,564,151 B1 | | 10/2013 | Huebner |
| 8,595,515 B1 | | 11/2013 | Weber et al. |
| 8,601,287 B1 | | 12/2013 | Weber et al. |
| 8,635,973 B1 | * | 1/2014 | Shepard, III ........... A01K 61/70 119/221 |
| 8,636,565 B2 | | 1/2014 | Carlson et al. |
| 8,700,929 B1 | | 4/2014 | Weber et al. |
| 8,774,980 B2 | | 7/2014 | Chang et al. |
| 8,780,542 B1 | | 7/2014 | Dariavach et al. |
| 8,839,254 B2 | | 9/2014 | Horvitz et al. |
| 8,849,469 B2 | | 9/2014 | Belady et al. |
| 8,853,872 B2 | | 10/2014 | Clidaras et al. |
| 8,854,809 B2 | | 10/2014 | Neumann et al. |
| 8,890,359 B2 | | 11/2014 | Chang |
| 8,913,383 B1 | | 12/2014 | Goldsmith et al. |
| 9,009,500 B1 | | 4/2015 | Fan et al. |
| 9,016,352 B2 | | 4/2015 | Helbig et al. |
| 9,063,738 B2 | | 6/2015 | Jain et al. |
| 9,089,078 B2 | | 7/2015 | Branton |
| 9,144,228 B1 | * | 9/2015 | Ortego ............... E02B 3/046 |
| 9,155,230 B2 | | 10/2015 | Eriksen |
| 9,207,993 B2 | | 12/2015 | Jain |
| 9,209,985 B1 | | 12/2015 | Wise |
| 9,287,710 B2 | | 3/2016 | Talkin et al. |
| 9,310,855 B2 | | 4/2016 | Godrich et al. |
| 9,342,375 B2 | | 5/2016 | Hyser et al. |
| 9,439,322 B1 | | 9/2016 | Magcale et al. |
| 9,439,330 B1 | | 9/2016 | Wu et al. |
| 9,439,331 B1 | | 9/2016 | Wu et al. |
| 9,450,838 B2 | | 9/2016 | Jain et al. |
| 9,595,054 B2 | | 3/2017 | Jain et al. |
| 9,648,777 B2 | | 5/2017 | Finn |
| 9,653,003 B2 | | 5/2017 | Laine et al. |
| 9,655,283 B2 | | 5/2017 | James et al. |
| 9,913,409 B2 | | 3/2018 | Cutler et al. |
| 2007/0281639 A1 | | 12/2007 | Clidaras et al. |
| 2008/0029250 A1 | | 2/2008 | Carlson et al. |
| 2008/0055846 A1 | | 3/2008 | Clidaras et al. |
| 2008/0055850 A1 | | 3/2008 | Carlson et al. |
| 2008/0209234 A1 | | 8/2008 | Clidaras et al. |
| 2009/0078401 A1 | | 3/2009 | Cichanowicz |
| 2009/0123758 A1 | * | 5/2009 | Amidaiji ............... C09D 5/08 428/413 |
| 2009/0216910 A1 | | 8/2009 | Duchesneau |
| 2009/0229194 A1 | | 9/2009 | Armillas |
| 2009/0293136 A1 | | 11/2009 | Campbell et al. |
| 2009/0295167 A1 | | 12/2009 | Clidaras et al. |
| 2009/0297270 A1 | | 12/2009 | Black et al. |
| 2010/0152501 A1 | * | 6/2010 | Oren ............... C07C 201/12 568/946 |
| 2010/0254087 A1 | * | 10/2010 | Godfroy ............... H05K 5/06 361/699 |
| 2010/0277719 A1 | | 11/2010 | Chen et al. |
| 2011/0132579 A1 | | 6/2011 | Best et al. |
| 2011/0144930 A1 | | 6/2011 | Bruno et al. |
| 2011/0154842 A1 | | 6/2011 | Heydari et al. |
| 2011/0176391 A1 | * | 7/2011 | DeLaCroix ............ A01K 79/02 367/139 |
| 2011/0240497 A1 | | 10/2011 | Dechene et al. |
| 2011/0247348 A1 | | 10/2011 | Mashiko et al. |
| 2012/0027154 A1 | | 2/2012 | Sugiura et al. |
| 2012/0232879 A1 | | 9/2012 | Iyengar et al. |
| 2013/0044426 A1 | | 2/2013 | Neumann et al. |
| 2013/0058029 A1 | | 3/2013 | Ootani et al. |
| 2013/0125825 A1 | | 5/2013 | Kania et al. |
| 2013/0190941 A1 | | 7/2013 | Cader et al. |
| 2014/0192708 A1 | | 7/2014 | Wise |
| 2014/0216686 A1 | * | 8/2014 | Shelnutt ............... H05K 7/20809 165/67 |
| 2014/0246174 A1 | | 9/2014 | Arvelo et al. |
| 2015/0059636 A1 | * | 3/2015 | Chezhian ............... B63B 39/06 114/349 |
| 2015/0194813 A1 | | 7/2015 | Finn |
| 2015/0321739 A1 | | 11/2015 | Dehlsen |
| 2015/0382511 A1 | | 12/2015 | James et al. |
| 2015/0382515 A1 | | 12/2015 | James et al. |
| 2016/0007577 A1 | * | 1/2016 | Constantz ............ A01K 63/065 119/245 |
| 2016/0012713 A1 | | 1/2016 | Siwak et al. |
| 2016/0076213 A1 | * | 3/2016 | Mefford ............... A01K 61/00 119/219 |
| 2016/0266246 A1 | | 9/2016 | Hjelmstad |
| 2016/0286695 A1 | | 9/2016 | Wu et al. |
| 2016/0378981 A1 | | 12/2016 | Cutler et al. |
| 2016/0381840 A1 | * | 12/2016 | Peterson ............... F24F 5/0046 361/679.46 |

(56) References Cited

U.S. PATENT DOCUMENTS

| | | |
|---|---|---|
| 2017/0023384 A1 | 1/2017 | Young |
| 2017/0083018 A1* | 3/2017 | Womble .............. A01K 27/009 |

FOREIGN PATENT DOCUMENTS

| | | | |
|---|---|---|---|
| CN | 201846435 U | 5/2011 | |
| CN | 102626006 A | 8/2012 | |
| DE | 102011115657 A1 | 3/2013 | |
| EP | 2891761 A2 | 7/2015 | |
| FR | 2578875 A1 * | 9/1986 | ............. E02B 3/046 |
| GB | 2004704 B | 1/1982 | |
| GB | 2240847 A | 8/1991 | |
| JP | 02091312 A * | 3/1990 | |
| JP | 02265421 A * | 10/1990 | |
| TW | I295725 B | 4/2008 | |
| WO | 2008039181 A1 | 4/2008 | |
| WO | 2009108070 A1 | 9/2009 | |
| WO | 2012129612 A1 | 10/2012 | |
| WO | 2013184820 A1 | 12/2013 | |
| WO | 2014120275 A1 | 8/2014 | |

OTHER PUBLICATIONS

"International Search Report and Written Opinion Issued in PCT Application No. PCT/US2016/063803", dated Apr. 3, 2017, 13 Pages.
Cutler, et al., "Artificial Reef Datacenter" U.S. Appl. No. 62/286,964, 19 pages.
Cutler, "Intrusion Detection for Submerged Datacenters" U.S. Appl. No. 62/286,961, 29 pages.
Trabish, Herman K., "Ocean Energy to Power Google's Sea-Going Data Center", Published on: Sep. 10, 2008, 4 pages Available at: http://newenergynews.blogspot.in/2008/09/ocean-energy-to-power-googles-sea-going.html.
Miller, Rich, "Google Planning Offshore Data Barges", Published on: Sep. 6, 2008, 5 pages Available at: http://www.datacenterknowledge.com/archives/2008/09/06/google-planning-offshore-data-barges/.
Miller, Rich, "Data Centers on Cargo Ships?", Published on: Jan. 8, 2008, 5 pages Available at: http://www.datacenterknowledge.com/archives/2008/01/08/data-centers-on-cargo-ships/.
"International Search Report & Written Opinion Received for PCT Application No. PCT/US2015/037848" dated Oct. 6, 2015, 10 pages.
Patel, et al., "Thermal Considerations in Cooling Large Scale High Compute Density Data Centers", In the Eighth Intersociety Conference on Thermal and Thermomechanical Phenomena in Electronic Systems, May 2002, 10 pages.
U.S. Appl. No. 13/917,636, Rubenstein, et al., "Renewable Energy Based Datacenter Cooling", filed Jun. 13, 2013, 31 pages.
Office Action Summary, U.S. Appl. No. 14/272,656, Notification Date: Nov. 30, 2015, 12 pages.
Green (Low Carbon) Data Center Blog, The Under Water Data Center, Response to Risks of Google's Floating Data Center, Submerge, Sep. 12, 2008, 3 pages. Available at: http://www.greenm3.com/gdcblog/2008/9/12/the-under-water-data-center-response-to-risks-googlersquo.html.
U.S. Appl. No. 14/272,656, Dehlsen, "Marine Subsurface Data Center Vessel", filed May 8, 2014, 16 pages.
"International Search Report & Written Opinion Received for PCT Application No. PCT/US2015/037847", dated Nov. 9, 2015, 11 pages.
Markoff, John, "Microsoft Plumbs Ocean's Depths to Test Underwater Data Center", Published on: Jan. 31, 2016, 5 pages. Available at: http://www.nytimes.com/2016/02/01/technology/microsoft-plumbs-oceans-depths-to-test-underwater-data-center.html?_r=2.
Callahan, Emily, "Artificial Reefing—The Blue Solution to America's Aging Infrastructure?", Published on: Nov. 6, 2014, 9 pages. Available at: http://voices.nationalgeographic.com/2014/11/06/artificial-reefing-the-blue-solution-to-americas-aging-infrastructure/.
Matteson, et al., "Maximizing Data Center Energy Efficiency by Utilizing New Thermal Management and Acoustic Control Methodology", In International Technical Conference and Exhibition on Packaging and Integration of Electronic and Photonic Microsystems, vol. 2, Jul. 16, 2013, 1 page.
Toma, et al., "Study on Heat Dissipation and Cooling Optimization of the Junction Box of OBSEA Seafloor Observatory", In Proceedings of IEEE/ASME Transactions on Mechatronics, vol. 20, Issue 3, Jun. 2015, pp. 1301-1309.
Masaki, et al., "Underwater Surveillance System to Counteract Associated Underwater Threats", In NEC Technical Journal, vol. 8, Issue 1, Sep. 2013, pp. 63-67.
Felemban, Emad, "Advanced Border Intrusion Detection and Surveillance Using Wireless Sensor Network Technology", In International Journal of Communications, Network and System Sciences, vol. 6, Issue 5, May 2013, pp. 251-259.
Casari, Paolo, "Using Sound to create Underwater Networks", Published on: May 29, 2015, 3 pages. Available at: http://phys.org/wire-news/194344776/using-sound-to-create-underwater-networks.html.
Murad, et al., "A Survey on Current Underwater Acoustic Sensor Network Applications", In International Journal of Computer Theory and Engineering, vol. 7, Issue 1, Feb. 2015, pp. 51-56.
Laumer, John, "Google Floats a Data Center Patent: Offshore, Ocean-Cooled, Wave-Powered, and Modular", Published on: Sep. 20, 2008, 4 pages. Available at: http://www.treehugger.com/corporate-responsibility/google-floats-a-data-center-patent-offshore-ocean-cooled-wave-powered-and-modular.html.
Fletcher, Joanna, "What Happened to Google's Floating Data Center?", Published on: Dec. 4, 2010, 2 pages. Available at: http://www.hostway.com/web-resources/find-web-hosting/what-happened-to-googles-floating-data-center/.
"Second Written Opinion Received for PCT Application No. PCT/US2015/037847", dated Jun. 1, 2016, 7 pages.
"International Preliminary Report on Patentability Received for PCT Application No. PCT/US2015/037847", dated Sep. 21, 2016, 6 pages.
"International Preliminary Report on Patentability Issued in PCT Application No. PCT/US2015/037848" dated Apr. 21, 2016, 6 pages.
"Non Final Office Action Issued in U.S. Appl. No. 15/167,808", dated Jul. 20, 2017, 22 Pages.
"International Search Report and Written Opinion Issued in PCT Application No. PCT/US2017/013621", dated Apr. 13, 2017, 14 Pages.
"Office Action Issued in European Patent Application No. 17704350.2", dated Jul. 23, 2019, 6 Pages.

* cited by examiner

ARTIFICIAL REEF DATACENTER

CLAIM OF PRIORITY

This application claims the benefit of U.S. Provisional Patent Application Ser. No. 62/286,964, entitled "Artificial Reef Datacenter" and filed on Jan. 25, 2016, U.S. Provisional Patent Application Ser. No. 62/286,961, entitled "Intrusion Detection for Submerged Datacenters" and filed on Jan. 25, 2016, U.S. patent application Ser. No. 14/752,669, entitled "Underwater Container Cooling Via Integrated Heat Exchanger" and filed on Jun. 26, 2015, and U.S. patent application Ser. No. 14/752,676, entitled "Underwater Container Cooling Via External Heat Exchanger" and filed on Jun. 26, 2015, all of which are incorporated herein by reference in their entirety for all intents and purposes.

SUMMARY

Examples of the disclosure provide for an apparatus for promoting marine life. The apparatus includes a datacenter implemented in a body of water and coupled to a network, a pressure vessel that houses the datacenter, and one or more components coupled to the pressure vessel that sustain a surrounding ecosystem.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

Corresponding reference characters indicate corresponding parts throughout the drawings.

DETAILED DESCRIPTION

Environmental concerns for the erosion of beaches, diminishing marine life, loss of active reefs, and other impacts have led to the installations of artificial reefs in some areas. Often, artificial reefs are built using objects originally made for another purpose, and repurposed into an artificial reef, such as oil rigs or decommissioned vehicles. However, these repurposed objects often introduce additional environmental concerns, such as corrosion and the introduction of pollutants into the marine environment.

In addition, these repurposed objects often provide a less than ideal environment for growth of reef inhabitants, or may promote some reef life more than others leading to an imbalance in the reef ecosystem. For example, oil rigs often emit heat providing a very warm surface, which may inhibit or otherwise challenge growth for some types of reef life.

Examples of the disclosure provide for an artificial reef datacenter. A datacenter configured for operation while submerged in water is designed to incorporate structural components and other features that actively promote marine life and attract growth of reef inhabitants. As used herein, active promotion of life may include, without limitation, active behaviors of the datacenter, such as providing warmth or dispersing nutrients in a surrounding environment, for example. Additionally, active promotion of life may include, without limitation, datacenter design and structural decisions, which lead to an inviting structure or components for colonization of marine life, for example. Because the artificial reef datacenter emits little to no heat differential in the surrounding environment, natural growth of diverse reef life is provided. Further, diverse and rapid growth of reef inhabitants is actively promoted due to the structural stability and environmental conditions provided by the datacenter.

Referring to the figures, examples of the disclosure are generally directed towards providing and/or deploying a datacenter (generally a facility comprising centrally managed computing resources and related support systems) as an artificial reef that is designed to be submerged, for example on the ocean floor or the floor of any similar deep body of water, such as a lake, river, flooded former quarry and so on. The datacenter may be deployed relatively close to current and potential customers, and positioned in a way to take advantage of sustainable power that is also environmentally friendly, and take advantage of the massive heat sink provided by the water. By positioning the datacenter in deep water, such as anchoring it or sinking it to the ocean floor, the risks of umbilical detachment or damage to the datacenter by external forces are significantly reduced. By providing the datacenter as an artificial reef, marine life is enhanced and marine life growth is promoted.

It should be understood that any of the examples herein are non-limiting. For example, ocean-submerged datacenters are exemplified, as is the concept of positioning datacenters on the ocean floor, such as by sinking them. However, bodies of water other than the ocean provide similar benefits, and anchoring rather than sinking may be used, such as if the ocean floor is too uneven at an otherwise desired location. As used herein, "floor" refers to the bottom of any body of water, e.g., the ocean floor, a riverbed, seabed, lake bottom and so on. As such, aspects of the disclosure are not limited to any particular embodiments, aspects, concepts, structures, functionalities or examples described herein. Rather, any of the embodiments, aspects, concepts, structures, functionalities or examples described herein are non-limiting, and the present disclosure may be used in various ways that provide benefits and advantages in datacenters and computing in general.

Aspects of the disclosure provide for a rich environment for marine life, by implementing an artificial reef datacenter designed for both computation and/or data storage, as well as growth of marine life. By providing structural elements and other components of the datacenter adapted to actively promote marine life, the artificial reef datacenter benefits both the local marine life and the local network usage needs on land or elsewhere.

Figure 1:
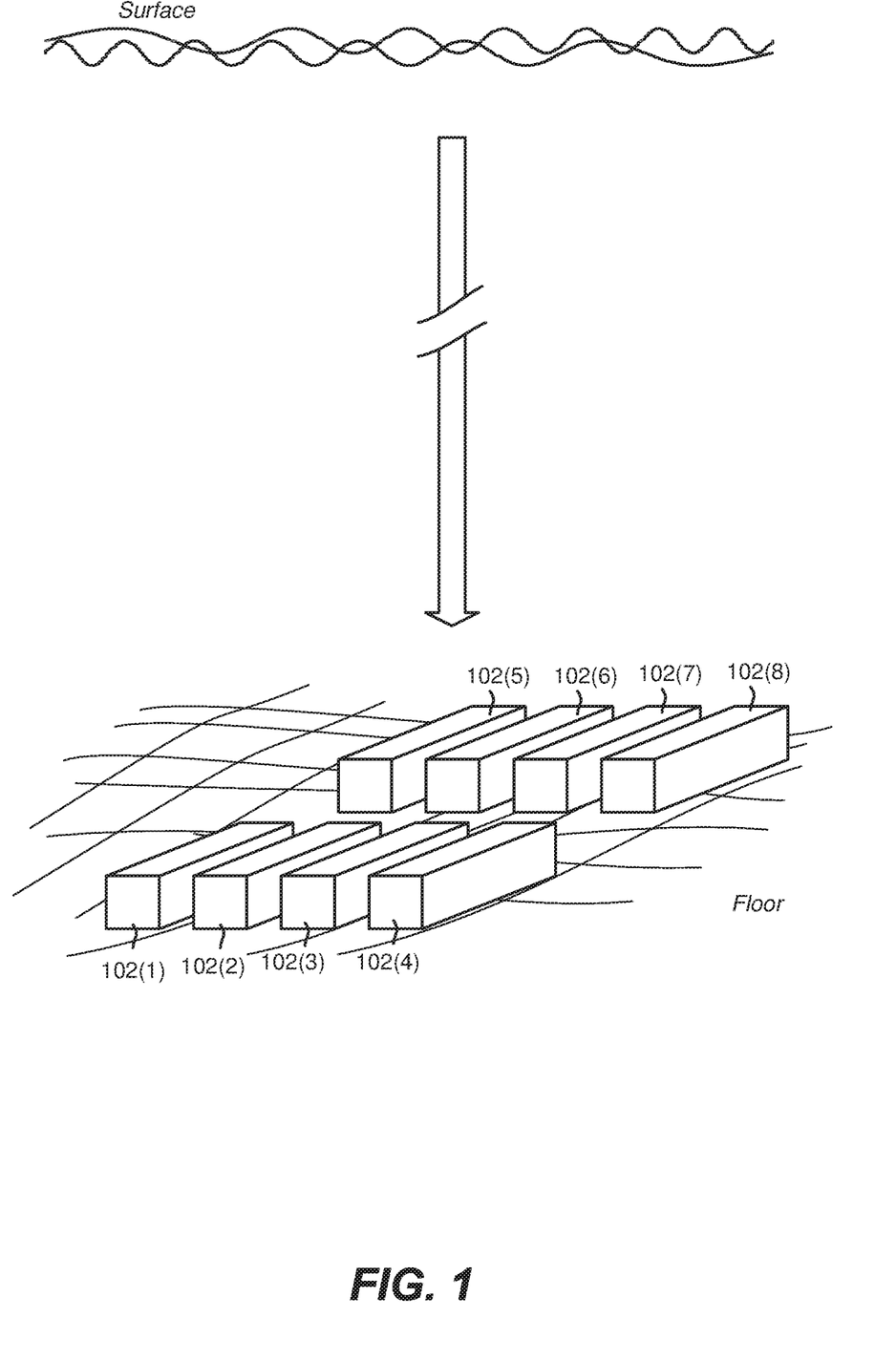
FIG. 1 is an exemplary block diagram illustrating a submerged datacenter resting on the floor of a body of water.

As generally represented in the example implementation of FIG. 1, a number of (e.g., modular) datacenter modules 102(1)-102(8) may be submerged to rest on the floor of any body of water. Modularity is not necessary, however modularity has some advantages, including being able to size a datacenter to different populations via using an appropriate number of modules, replacement at the end of a module lifecycle, portability, security (e.g., modules can be divided into public modules or private modules, with no communication between them, and so on.) Further, modularity allows for ease of manufacturing and may speed up datacenter deployment while lowering the prices.

With respect to deployment, a datacenter module may be towed or otherwise conveyed to its desired location, coupled to cabling and any other datacenter modules, and sank in any number of ways, such as by attaching weight, adding water to a ballast tank, and so forth. In the event that the datacenter module may need service or replacement, the weight may be removed to allow the datacenter to float. Note that at depths below conventional human diving capability, machinery may be used to remove the weight or attach a pipe to pump air in and the water out of the ballast tank. In other examples, inflatable components may be affixed to or around the datacenter or portions of the datacenter, and inflated when the datacenter or portions of the datacenter are to be accessed. Similarly, any components that are more likely to need servicing, such as those with moving parts like pumps, may benefit from redundancy and/or be designed to be detachable or removable.

Figure 2:
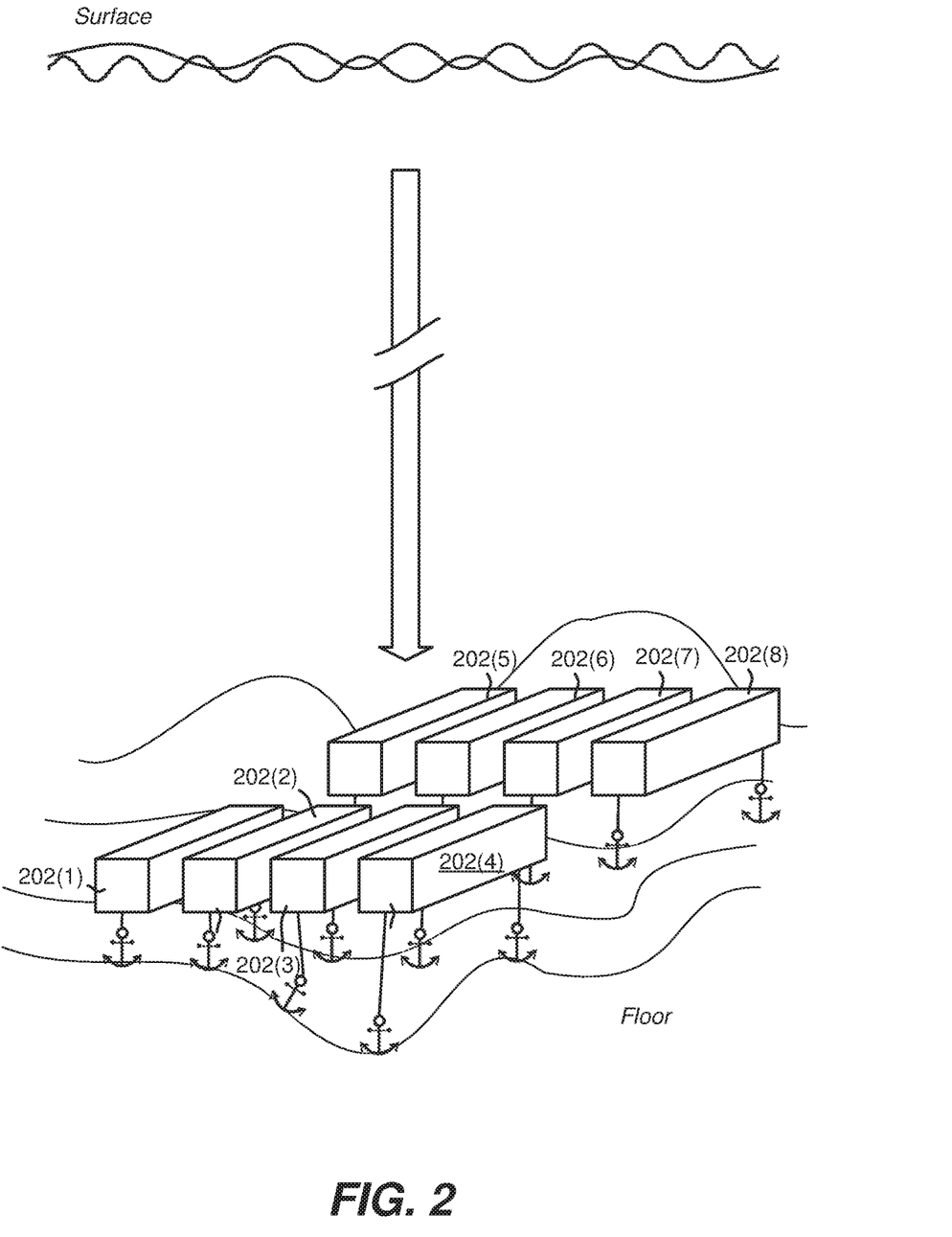
FIG. 2 is an exemplary block diagram illustrating a submerged datacenter anchored to the floor of a body of water.

FIG. 2 shows an alternative implementation, in which datacenter modules 202(1)-202(8) are slightly buoyant on their own, but via anchoring are anchored to the floor in a desired orientation and pattern, e.g., level and evenly distributed in a line or arrayed pattern. As can be readily appreciated, anchoring facilitates deployment of datacenters to floors with irregular terrain. Note that the depths may be pre-mapped so that the anchor chains or the like may be designed with a suitable length to keep the datacenters at a desired orientation. In general, a submerged datacenter may be securely anchored (by its own weight as in FIG. 1 or by heavy attached weight as in FIG. 2) to avoid shifting position and detaching from any (electrical and fiber internet) service cabling. In other examples, the anchoring system itself may be another artificial reef.

As is understood, the depiction of eight modules in FIGS. 1 and 2 is an arbitrary number merely for purposes of illustration. For example, a single datacenter may be submerged, (which may not be modular), up to any practical number.

Cabling is not shown in FIGS. 1 and 2, but as is understood, a power source and data communication connections, such as fiber optics, may be coupled to each datacenter module. Moreover, any or all of the datacenter modules, e.g., 102(1)-102(8) or 202(1)-202(8), may be coupled to one another for highly efficient internal communication including by any wired or wireless connections. In the event that power is coming from land, the cabling may be arranged such that a single jacket surrounds both the power cable and fiber optic communication cabling, whereby only one reel may be used, and the different cables cannot get in each other's way during deployment. Further, at least some of the communication signals may be transmitted/received through the power cable.

Figure 3:
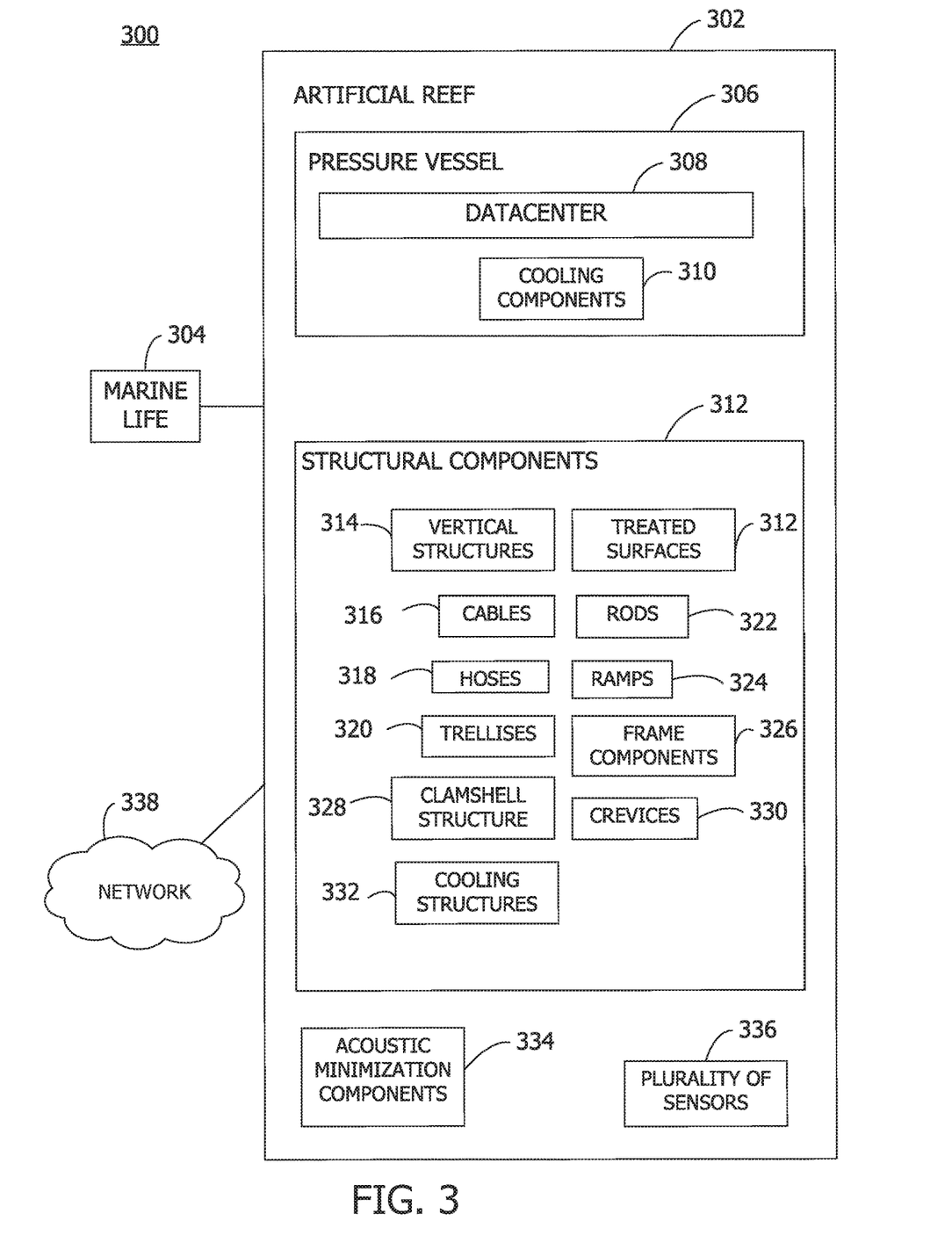
FIG. 3 is an exemplary block diagram illustrating an artificial reef environment.

FIG. 3 depicts an artificial reef environment 300. Artificial reef 302 may be deployed underwater to attract, promote, enhance, and/or otherwise enrich marine life 304, and the underwater environment. Artificial reef 302 may include pressure vessel 306, which may house datacenter 308 and cooling components 310. Data center 308 is implemented in a body of water as an artificial reef. In some examples, pressure vessel 306 may be a removable portion of artificial reef 302, and datacenter 308 may be implemented across multiple pressure vessels, such that removal of one pressure vessel is not removal of the entire datacenter, but rather a portion of the datacenter. In other words, datacenter 308 may be implemented across a plurality of datacenter units, such as across multiple pressure vessels, to provide a plurality of datacenter units configured as an artificial reef to be implemented in a body of water.

Artificial reef 302 may include structural components 312, which may be adapted to provide for the reef structure and active support of reef growth and marine life. For example, structural components 312 may include treated surfaces 312, vertical structures 314, cables 316, hoses 318, trellises 320, rods 322, ramps 324, frame components 326, clamshell structure 328, crevices 330, cooling structures 332, and/or any other suitable components or structures adapted to promote reef life. Artificial reef 302 may also include acoustic minimization components 334 and plurality of sensors 336. Artificial reef 302 may be in communication with or otherwise coupled to network 338, in this example. Network 338 may be a local network, in some examples, supported by datacenter 308.

The external surfaces and structures of the datacenter may actively promote the colonization of the datacenter by marine life, sustaining or enriching the surrounding ecosystem. For example, because some external surfaces of the datacenter have minimal heat transfer or exchange, these surfaces may have a temperature that is at most a couple of degrees (Celsius) different than surrounding environmental temperatures, which may promote growth rather than slow or inhibit growth as very warm surfaces have been shown to do. Additionally, means of promoting the presence of marine life and utilization of the data center as an artificial reef may include vertical or other surfaces to seed plankton and other marine life that benefits from nutrient-rich upwellings or use of appropriately roughened or treated surfaces to promote the adhesion of microscopic life, such as algae and bacteria, both of which attract next stage predators on the food chain. It has been observed that in some instances a new artificial reef can be detrimental to existing natural or artificial reefs by, for example, selectively attracting a subset of nearby species in such a way that the surrounding ecosystem on or near an existing reef is impacted even as the new reef thrives. Datacenters may be specifically tailored for the surrounding ecosystem to ensure the health of both the preexisting surrounding ecosystem and its extension to the datacenter by thoughtful design and planning, in order to avoid selective migration of local species to the datacenter that may negatively impact the surrounding ecosystem.

Structural components, such as holes and crevices, provide for marine life seeking such protective habits, including, without limitation, grouper, eel, and snapper, for example. Electro-mineral accretion applied to metallic exterior surfaces of the datacenter may promote the crystallization of limestone on the surfaces of the datacenter, to which coral planulae attach and grow. Cables, rods, hoses, or ramps enable non-swimming marine life to climb or otherwise traverse the datacenter. Structures such as exterior trellises may also be incorporated into the datacenter explicitly to serve as or enhance the artificial reef. Various structural components may be coupled together to form the artificial reef, such as by screws, etching, bolts, clamps, or otherwise attached or affixed in order to provide the artificial reef structure.

At least some portion of the surface structures may be removable on a temporary or permanent basis while maintaining the reef present on those structures that remain in the water when the datacenter is retrieved for maintenance or retirement to reduce the impact on the ecosystem of said maintenance or retirement.

The datacenter may be encased in a shell, such as a clamshell configuration. In this example, any cooling surfaces of the datacenter which are in direct contact with open ocean water may maintain exposure to open ocean water while other surfaces are implemented within the shell. When the datacenter is retrieved for maintenance or retirement, the datacenter is removed from its casing, or shell, and the casing remains behind in the ocean. In this example, the datacenter itself stays largely unaffected by the growth of marine life, but is surrounded by or embedded within structure or structures that serve as the permanent artificial reef. In this way, minimum disruption to the ecosystem is provided when a datacenter is retrieved for service or replacement because the growing reef remains in the water.

At least a portion of the cooling surfaces or structures of the artificial reef are configured or otherwise treated to prevent, or at least impede, the colonization of these cooling surfaces by marine life. Colonization of cooling surfaces, such as external heat exchangers may reduce the ability to cool the datacenter as required for operation. Some examples of preventing or impeding colonization on these specific surfaces may include: anti-stick coatings such as highly hydrated zwitterions, those which create hydrophobic surfaces, or the emerging class of biomimetic coatings which prevent microorganisms from attaching to surfaces, or only allows them to attach weakly, allowing natural water current to carry away any adhering organisms before a significant biofilm is formed. Additionally, physical brushing of cooling surfaces using a wire brush or similar instrument; bathing cooling surfaces in UV light provided by LEDs to prevent the growth of microorganisms; LEDs spaced at regular intervals across the surface of each cooling surface, or on a separate panel facing a cooling surface (like lights in a sports stadium) to keep the entire cooling surfaced bathed in UV light; a water jet applied to the cooling surfaces, which may be built into the datacenter or provided by divers or by an ROV (remotely operated vehicle) from the surface or attached to the datacenter; ultrasonic transducers placed within external heat exchangers focusing energy at the external surfaces of such heat exchangers or alternatively ultrasonic transducers placed within the datacenter and focused at the external surfaces of the datacenter where such datacenter's external walls contain integrated heat exchanger. The ultrasonic energy kills or denatures the first stage biofouling organisms forming on the external surface. The use of electric current, electro hydrolyzing, or very brief plasma charges to kill biofouling may also be used, as well as chlorine-based anti-fouling systems that dispense chlorine to attack biofouling. Other methods may include copper-containing cooling surfaces or copper-containing anti-fouling coatings or biocide-based anti-fouling coatings applied to the cooling surfaces.

Acoustic minimization components 334 are designed to minimize the introduction of acoustic energy into the surrounding water for the protection of mammals and other sensitive marine life. Acoustic minimization components may include active noise cancellation systems, either internal or external, or both, to the data center housing or vessel, in some examples. For example, through the use of anti-vibration mounts with mechanical components such as pumps, fans, motors, and rotational disk drives to isolate them from the external structure of the pressure vessel. In other examples, dynamic vibration absorbers or tuned mass dampeners with rotational mechanical components such as fans, pumps, motors, and rotational disk drives to cancel or reduce harmonic vibration. Still, other examples include the use of acoustic foam applied inside the data center modules on the exterior walls which interface to the ocean. Acoustic foam serves to attenuate airborne sound waves, reducing the amplitude of the sound waves before they reach the exterior walls.

Some other examples of acoustic minimization components include design or selection of data center structural components and exterior walls which exhibit minimal resonance when stimulated by the vibration of mechanical components within the data center, whether resonant energy is imparted by physical connection (e.g., motor to frame to exterior wall) or via conduction of sound waves through the internal atmosphere of the data center. Additionally, choice of operating frequencies of mechanical components to spread the resonant energy across multiple frequencies to limit the energy imparted to any particular frequency, or more specifically to minimizing acoustic energy emissions at frequencies to which marine life is sensitive may be used.

Plurality of sensors 336 may allow monitoring the health of the reef in real time and over long periods of time. The output of, or control over, these sensors may optionally be made available to the data center owner, data center customers, or the general public via network 338 communicatively coupled to the artificial reef datacenter. For example: cameras, including high resolution color cameras, to directly observe the environment. Cameras may include their own sources of illumination. Other sensors may include sensors to detect and/or monitor water salinity, current, temperature, pH, oxygen content, turbidity, electrical conductivity, and acoustic emanations.

Figure 4:
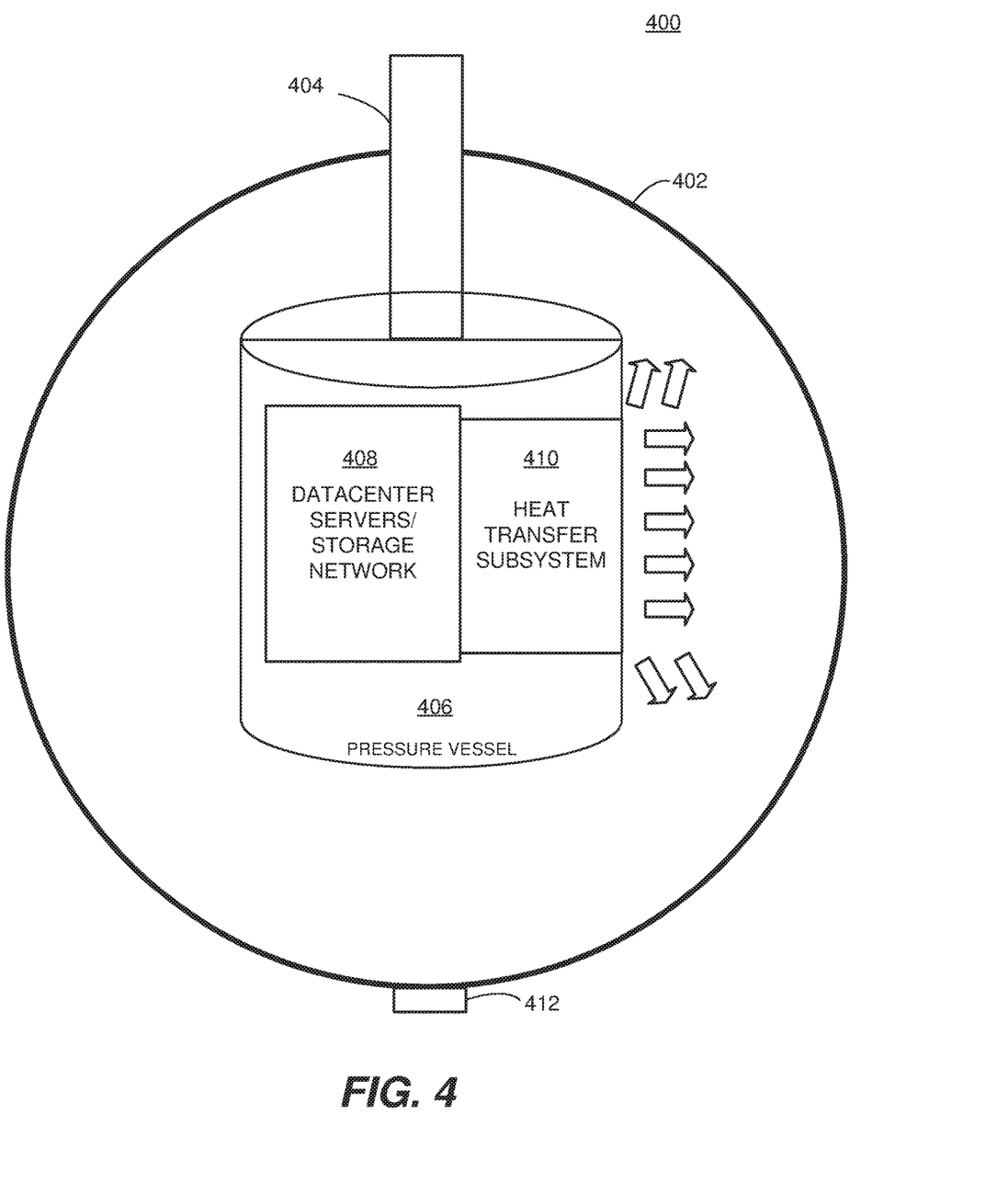
FIG. 4 is an exemplary block diagram illustrating an artificial reef datacenter.

FIG. 4 depicts one example implementation of an artificial reef datacenter. Artificial reef datacenter 400 includes clamshell 402, access point 404, and pressure vessel 406. Clamshell 402 may be an illustrative example of one implementation of an encasement surrounding a removable portion of the datacenter, where the encasement is configured to allow access to the removable portion of the datacenter as the artificial reef is maintained.

Pressure vessel 406 may house datacenter 408 and heat transfer subsystem 410. In some examples, pressure vessel 406 may be a removable portion of artificial reef datacenter 400, and datacenter 408 may be an illustrative example of a portion of a datacenter implemented across multiple pressure vessels of an artificial reef datacenter, such that removal of one pressure vessel is not removal of the entire artificial reef datacenter, but rather a portion of the datacenter. In some examples, a plurality of encasements, such as clamshell 402, may individually house one or more of the plurality of datacenter units that make up an artificial reef datacenter.

Datacenter 408 may include servers and/or storage networks of artificial reef datacenter 400. Heat transfer subsystem 410 transfers heat away from datacenter 408 to the surrounding air within pressure vessel 406 and/or for use in power generation. Heat transfer subsystem 410 may include, without limitation, coils, radiators, fluid pumps, fans, or any other suitable component. The hot air coming from the servers of datacenter 408 is received by heat exchangers of heat transfer subsystem 410 and absorbed away from datacenter 408, with heat transfer subsystem 410 emitting cool air in return towards datacenter 408. This heat exchange may be achieved via liquid flowing through heat exchangers of heat transfer subsystem 410, in some examples, with the liquid absorbing the heat and emitting cool air. The liquid may be circulated in a sealed, closed loop heat exchange within heat transfer subsystem 310, in these examples. Because the heat exchange is provided as a sealed cooling loop within pressure vessel 406, there is no issue with debris or other matter that may otherwise impact the cooling function of heat transfer subsystem 410 being introduced into the cooling loop.

Heat transfer subsystem 410 may also have a second loop, or second subset of heat exchangers, which may take the heat absorbed from the first loop into the surrounding air or liquid and transfer that heat away from the pressure vessel 406 to the surrounding environment outside of pressure vessel 406, such as the sea water for example. This second heat exchange may transfer heat away from the environment of the pressure vessel housing the datacenter and into the surrounding environment, which may be without the encasement 402 in some examples, or may be outside of the encasement 402 in other examples.

Datacenter 408 may be housed within pressure vessel 406 implemented within clamshell 402 and accessible via access point 404. Heat transfer subsystem 410 may be partially implemented within pressure vessel 406 and partially implemented outside of pressure vessel 406, such as with a first subset of heat exchangers implemented within the pressure vessel and a second subset of heat exchangers implemented outside of the pressure vessel. Hinge 412 may operate to allow minimal movement of clamshell 402 to provide for removal of pressure vessel 406 via access point 404, in some examples. By allowing minimal movement during interaction with access point 404, the surrounding ecosystem and reef life associated with artificial reef datacenter 400 is maintained while still providing access to or removal of datacenter 408. Pressure vessel 406 may be temporarily removed from artificial reef datacenter 400 for maintenance or service, in some examples, or in order to repair or replace one or more components of datacenter 408, for example.

Figure 5:
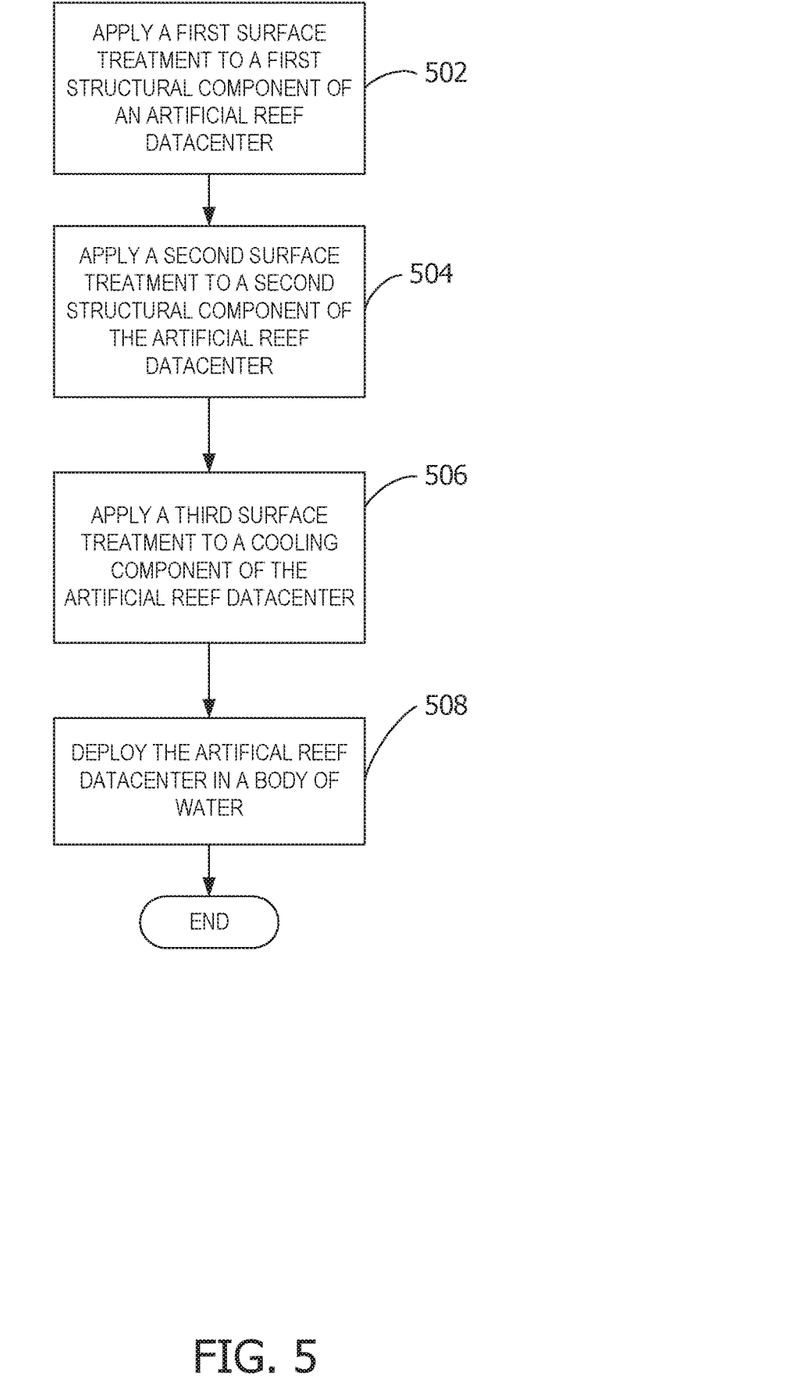
FIG. 5 is an exemplary flow chart illustrating operation to configure and deploy the artificial reef datacenter.

FIG. 5 depicts operations to apply a first surface treatment to a first structural component of an artificial reef datacenter at 502. The first surface treatment may be any suitable adaptation of a component of the datacenter in order to actively promote reef life. For example, the treatment may be an electro-mineral accretion, or an abrasive treatment or etching to roughen the surface. The first treatment may be configured to actively promote adhesion of microscopic life to the first structural component.

At 504 a second surface treatment is applied to a second structural component of the artificial reef datacenter. The second surface treatment may be any suitable adaptation of a component of the datacenter in order to actively promote reef life. The second surface treatment may be configured to actively promote colonization of reef life adjacent to the second structural component or at the second structural component. Various individual components of the artificial reef datacenter may be individually treated to promote different variations of reef life or to actively promote different degrees of growth, in some examples.

A third surface treatment is applied to a cooling component of the datacenter at 506. The third surface treatment may be configured to impede growth of microscopic life or colonization by reef life to the cooling component of the datacenter, in order to mitigate any impact on cooling and heat exchange for the datacenter. Upon appropriate treatment and adaptation of the structural components, the artificial reef datacenter is deployed into a body of water at 508. The datacenter may be secured to a floor of the body of water, such as an ocean floor in some examples, by anchoring or otherwise affixing the datacenter to the floor in such a way as to minimize movement or shifting and support active growth of reef life for the surrounding ecosystem.

Figure 6:
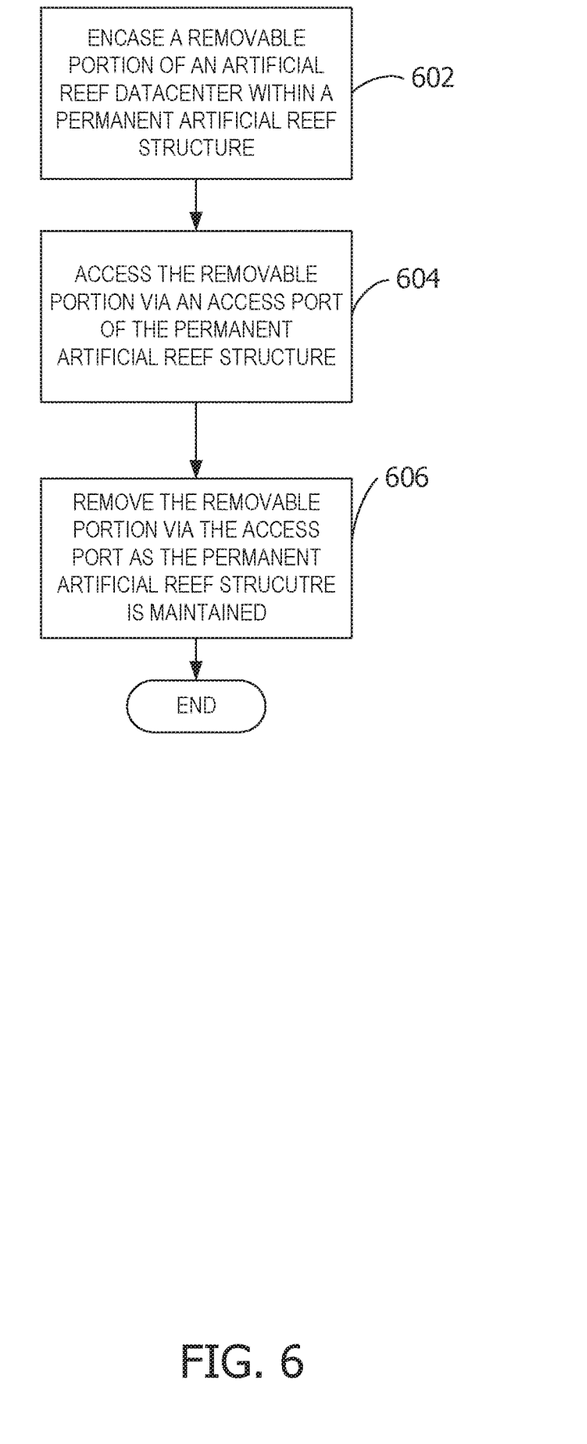
FIG. 6 is an exemplary flow chart illustrating operation to access and remove a portion of the artificial reef datacenter.

FIG. 6 depicts operations to access and remove a portion of an artificial reef datacenter. A datacenter, such as datacenter 408 in FIG. 4, is encased in a removable portion of an artificial reef datacenter within a permanent artificial reef structure at 602. The removable portion of the artificial reef datacenter may be a pressure vessel, such as pressure vessel 406 in FIG. 4, for example. The permanent artificial reef structure may be an encasement, such as encasement 402 in FIG. 4, for example. The permanent artificial reef structure may be secured to a floor of the body of water upon deployment, for example.

The removable portion of the artificial reef datacenter is accessed via an access port of the permanent artificial reef structure at 604. Access may be for maintenance, replacement, or removal or one or more components of the datacenter, for example. The access port may allow for minimal disruption to any reef life maintained by the permanent artificial reef structure, such that access to or removal of the removable portion is achieved while maintaining the artificial reef.

The removable portion is removed via the access port as the permanent artificial reef structure is maintained at 606, with the process terminating thereafter. In some examples, such as with the clamshell configuration of the encasement, the clamshell encasement may be moveably operated to open in such a way as to provide access via the access port while maintaining any reef life provided by or sustained by the clamshell encasement.

Additional Examples

Among other advantages of submerged datacenters, a large percentage of the world's population lives near the ocean or other relatively deep body of water, whereby submerging the datacenter provides close positioning of the datacenters to users, e.g., customers and/or a private enterprise's employees. Further, unlike floating datacenters, advantages are obtained from being below the water surface, particularly at a relatively deep depth. For example, floating datacenters are exposed to a variety of risks that can cause loss of power and service connections, including being prone to weather (ocean storms, wind, waves, floating objects, electrical strikes), tidal and ocean currents that cause normal ocean swell (which stress the connections to electrical power and the fiber internet backbone), accidents from commercial shipping, fishing and pleasure boat traffic, being easy to spot from the air or ocean surface and thus easier to target and/or board, increasing the risk of piracy, vandalism, sabotage or espionage.

Still other advantages include that for privacy and security concerns, some governments specify that their cloud services data be stored in their own country. Serving multiple countries from a Regional "Mega-Datacenter" is thus not always an option. At other times it may be advantageous to deploy a datacenter in international waters.

Any number of ways to provide power to a submerged datacenter may be used, including running power from conventional land-based sources. However, there are also opportunities to use power sources deployed in water, including ocean-based power sources such as power generated from tidal or ocean currents; in general, it reduces cost to generate power near its usage.

While the aspects of the disclosure have been described in terms of various examples with their associated operations, a person skilled in the art would appreciate that a combination of operations from any number of different examples is also within scope of the aspects of the disclosure. Additionally, one skilled in the art will appreciate that the various embodiments and methods described herein can be implemented in connection with any number of hardware devices and/or components, which can be deployed as part of a datacenter or other computing environment, and can be connected to any kind of data store or stores. Thus, the technology is not limited to a datacenter in the conventional sense, but may be used in any situation where computing power is needed near a certain location and underwater life is a consideration.

Alternatively, or in addition to the other examples described herein, examples include any combination of the following:
  one or more components are treated to actively promote adhesion of microscopic life;
  wherein the one or more surfaces include vertical or other surfaces that seed plankton and other marine life that benefits from nutrient-rich upwellings;
  wherein the one or more components include roughened surfaces that promote the colonization of reef life;
  one or more components configured to sustain a surrounding ecosystem;
  wherein the one or more components include holes or crevices that provide protective structures for at least some marine life;
  wherein the one or more components include at least one of cables, rods, hoses, or ramps that enable non-swimming marine life to climb or otherwise traverse the datacenter;
  wherein the pressure vessel is removable, and wherein the one or more components coupled to the pressure vessel are detachable from the pressure vessel;
  an encasement surrounding the pressure vessel, wherein the encasement is configured to allow access to the pressure vessel as an artificial reef, sustained by the one or more components, is maintained;
  one or more cooling components coupled to at least one of the datacenter or the pressure vessel;
  wherein at least a portion of the one or more cooling components impede colonization of marine life on the said portion of the one or more cooling components;
  one or more acoustic energy minimization components;
  wherein the one or more acoustic energy minimization components include anti-vibration mounts implemented in association with mechanical components of the datacenter to isolate an impact of the mechanical components from the external structure of the apparatus;
  wherein the one or more acoustic energy minimization components include at least one of dynamic vibration absorbers, tuned mass dampeners, or acoustic foam;
  one or more sensors coupled to the network and configured to monitor health of the surrounding ecosystem;
  wherein the encasement is moveably operated to provide access to the datacenter via an access point;
  one or more surfaces adapted to actively promote the colonization of the artificial reef by reef life;
  encasing a removable portion of the datacenter within a permanent structure;
  securing the permanent structure to a floor of the body of water upon deploying the datacenter;
  accessing the removable portion via an access port of the permanent structure;
  removing the removable portion via the access port as the permanent structure is maintained at the floor of the body of water.

While the aspects of the disclosure have been described in terms of various examples with their associated operations, a person skilled in the art would appreciate that a combination of operations from any number of different examples is also within scope of the aspects of the disclosure.

Exemplary Operating Environment

Figure 7:
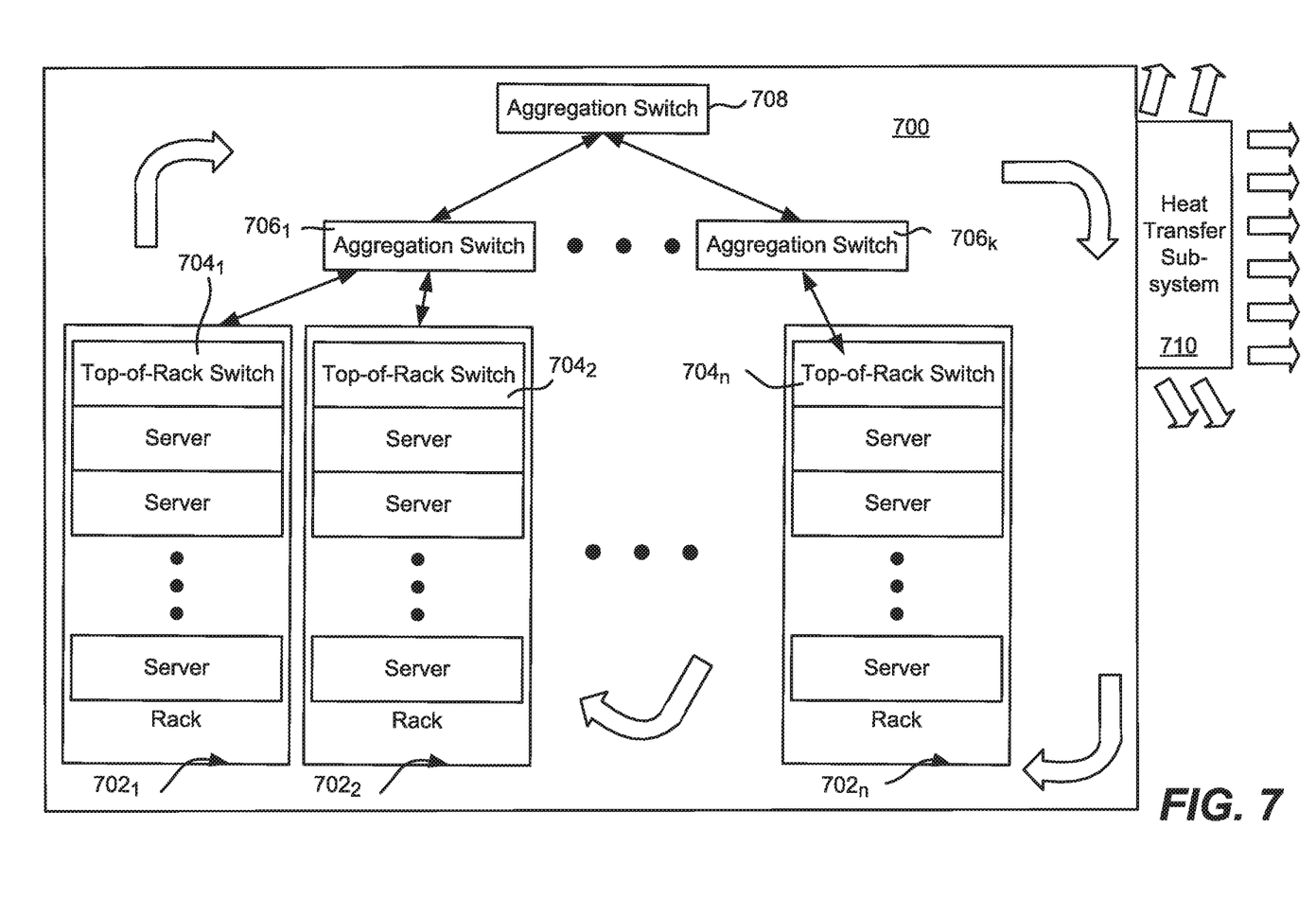
FIG. 7 is an exemplary block diagram illustrating a submerged datacenter environment in which one or more aspects of various examples described herein may be implemented.

FIG. 7 shows an example submerged datacenter 7000 (or one datacenter module) that is exemplified as having a tree-like topology. A plurality of racks $7002_1$-$7002_n$ each have servers, which communicate through a top of rack switch $7004_1$-$7004_n$. The servers may include storage, or at least part of the storage may be separately located. A typical network has twenty to forty servers per rack, with increasingly powerful links and switches going up the tree. Note that datacenters are not limited to tree-like topologies, but can be used in any topology. A small amount of the computing power may be used to monitor the submerged datacenter sensors, run any fans, pumps and so on, operate an active leveling system, and so on, although this may be done with separate machine logic.

As represented in FIG. 7 by the rounded arrows, the exemplified datacenter has gas and/or dielectric fluid circulated throughout, which may be via pumps, fans and/or natural circulation. A heat transfer subsystem 710, which may use coils, radiators, fluid pumps, fans and so forth transfers heat away from the datacenter/module to the surrounding water and/or for use in power generation. Note that a module's or datacenter's hull itself may be used as a heat transfer mechanism.

The order of execution or performance of the operations in examples of the disclosure illustrated and described herein is not essential, unless otherwise specified. That is, the operations may be performed in any order, unless otherwise specified, and examples of the disclosure may include additional or fewer operations than those disclosed herein. For example, it is contemplated that executing or performing a particular operation before, contemporaneously with, or after another operation is within the scope of aspects of the disclosure.

When introducing elements of aspects of the disclosure or the examples thereof, the articles "a," "an," "the," and "said" are intended to mean that there are one or more of the elements. The terms "comprising," "including," and "having" are intended to be inclusive and mean that there may be additional elements other than the listed elements. The term "exemplary" is intended to mean "an example of." The phrase "one or more of the following: A, B, and C" means "at least one of A and/or at least one of B and/or at least one of C."

The examples illustrated and described herein as well as examples not specifically described herein but within the scope of aspects of the disclosure constitute exemplary means for providing an artificial reef datacenter, exemplary means for treating surfaces of one or more structural components of the artificial reef datacenter to actively promote reef life, exemplary means for deploying an artificial reef datacenter into a body of water, and exemplary means for accessing and/or removing a removable portion of the artificial reef datacenter via an access port as a permanent artificial reef structure is maintained.

Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matter contained in the above description and shown in the accompanying drawings shall be interpreted as illustrative and not in a limiting sense.

What is claimed is:

1. An artificial reef submerged underwater for promoting marine life, the artificial reef comprising:
   one or more anchors that affix the artificial reef to a floor of a body of water;
   a datacenter comprising a plurality of servers aggregated through one or more switch and data communication connections coupled to a network;
   a pressure vessel that houses the datacenter and one or more cooling components, wherein at least a portion of the one or more cooling components is pretreated with one or more anti-stick coatings that impede colonization of marine life thereon; and
   one or more components coupled to the pressure vessel, the one or more components configured to actively promote reef life and sustain a surrounding ecosystem; and
   an encasement surrounding the pressure vessel, wherein the encasement is configured to allow removal of the pressure vessel as the encasement remains submerged.

2. The artificial reef comprising of claim 1, wherein the one or more components are treated to actively promote adhesion of microscopic life.

3. The artificial reef comprising of claim 1, wherein the one or more components include surfaces that seed plankton and other marine life that benefits from nutrient-rich upwellings.

4. The artificial reef comprising of claim 1, wherein the one or more components include roughened surfaces that promote the colonization of marine life.

5. The artificial reef comprising of claim 1, wherein the one or more components include holes or crevices that provide protective structures for at least some marine life.

6. The artificial reef comprising of claim 1, wherein the one or more components include at least one of cables, rods, hoses, or ramps that enable non-swimming marine life to climb or otherwise traverse the artificial reef.

7. The artificial reef comprising of claim 1, wherein the one or more components coupled to the pressure vessel are detachable from the pressure vessel.

8. The artificial reef comprising of claim 1, further comprising:
   one or more acoustic energy minimization components.

9. The artificial reef comprising claim 8, wherein the one or more acoustic energy minimization components include anti-vibration mounts implemented in association with mechanical components of the datacenter to isolate an impact of the mechanical components from an external structure of the artificial reef.

10. The artificial reef comprising claim 8, wherein the one or more acoustic energy minimization components include at least one of dynamic vibration absorbers, tuned mass dampeners, and acoustic foam.

11. The artificial reef comprising of claim 1, further comprising:
    one or more sensors coupled to the network and configured to monitor health of the surrounding ecosystem.

12. The artificial reef comprising of claim 1, wherein the anti-stick coatings is hydrophobic.

13. The artificial reef comprising of claim 1, further comprising:
    at least one water jet, aimed at the portion of the one or more cooling components, emitting water at a velocity that removes marine life.

14. The artificial reef comprising of claim 1, further comprising:
    one or more remotely operated vehicles adapted to remove colonization of marine life on the portion of the one or more cooling components.

15. The artificial reef comprising of claim 1, further comprising:
    an electrifying transducer coupled to the portion of the one or more cooling components emitting an electric current of an ampere that impedes colonization of marine life.

16. The artificial reef comprising of claim 1, further comprising:
    a plasma charging transducer coupled to the portion of the one or more cooling components emitting a degree of ionization that impedes colonization of marine life.

17. The artificial reef comprising of claim 1, wherein the anti-stick coatings comprises copper.

18. The artificial reef comprising of claim 1, the encasement is a clam shell encasement that includes at least a hinge configured to rotate the clam shell encasement and provide removal of the pressure vessel via an access point of the clam shell encasement as the clam shell encasement remains submerged.

19. An artificial reef submerged underwater for promoting marine life, the artificial reef comprising:
    one or more anchors that affix the artificial reef to a floor of a body of water;
    a datacenter comprising a plurality of servers aggregated through one or more switch and data communication connections coupled to a network;
    a pressure vessel that houses the datacenter and one or more cooling components, wherein at least a portion of the one or more cooling components is pretreated with one or more anti-stick coatings that impede colonization of marine life thereon; and
    one or more components coupled to the pressure vessel, the one or more components configured to actively promote reef life and sustain a surrounding ecosystem, wherein the one or more components are treated to actively promote adhesion of microscopic life; and
    an encasement surrounding the pressure vessel, wherein the encasement is configured to allow removal of the pressure vessel as the encasement remains submerged.

20. An artificial reef submerged underwater for promoting marine life, the artificial reef comprising:
    one or more anchors that affix the artificial reef to a floor of a body of water;
    a datacenter comprising a plurality of servers aggregated through one or more switch and data communication connections coupled to a network;
    a pressure vessel that houses the datacenter and one or more cooling components, wherein at least a portion of the one or more cooling components is pretreated with one or more anti-stick coatings that impede colonization of marine life thereon; and
    one or more components coupled to the pressure vessel, the one or more components configured to actively promote reef life and sustain a surrounding ecosystem, wherein the one or more components are treated to actively promote adhesion of microscopic life; and a clam shell encasement surrounding the pressure vessel, wherein the clam shell encasement includes at least a hinge configured to rotate the clam shell encasement and provide removal of the pressure vessel via an access point of the clam shell encasement as the clam shell encasement remains submerged.

\* \* \* \* \*